(12) United States Patent
Atarot et al.

(10) Patent No.: US 11,547,285 B2
(45) Date of Patent: Jan. 10, 2023

(54) SUPPORT AND POSITIONER FOR AN ENDOSCOPE MANEUVERING SYSTEM

(71) Applicant: GREAT BELIEF INTERNATIONAL LIMITED, Tortola (VG)

(72) Inventors: Gal Atarot, Kfar Saba (IL); Shlomi Karvat, Moshav Ramat Zvi (IL)

(73) Assignee: GREAT BELIEF INTERNATIONAL LIMITED, Tortola (VG)

( * ) Notice: Subject to any disclaimer, the term of this patent is extended or adjusted under 35 U.S.C. 154(b) by 412 days.

(21) Appl. No.: 14/650,315

(22) PCT Filed: Jan. 8, 2014

(86) PCT No.: PCT/IL2014/050022
§ 371 (c)(1),
(2) Date: Jun. 8, 2015

(87) PCT Pub. No.: WO2014/108898
PCT Pub. Date: Jul. 17, 2014

(65) Prior Publication Data
US 2015/0366433 A1    Dec. 24, 2015

Related U.S. Application Data

(60) Provisional application No. 61/749,942, filed on Jan. 8, 2013.

(51) Int. Cl.
*A61B 1/00* (2006.01)
*A61B 90/50* (2016.01)
*A61B 34/30* (2016.01)

(52) U.S. Cl.
CPC ........ *A61B 1/0016* (2013.01); *A61B 1/00149* (2013.01); *A61B 90/50* (2016.02); *A61B 2034/301* (2016.02)

(58) Field of Classification Search
CPC ............ A61B 1/00147; A61B 1/00149; A61B 1/00151; A61B 1/00154; A61B 1/00158;
(Continued)

(56) References Cited

U.S. PATENT DOCUMENTS 5,441,042 A * 8/1995 Putman .................. B25J 9/042
600/102
6,632,170 B1    10/2003 Bohanan et al.
(Continued)

OTHER PUBLICATIONS

International Search Report and Written Opinion dated May 12, 2014 in co-pending International Application No. PCT/IL2014/50022.

*Primary Examiner* — Ryan N Henderson
*Assistant Examiner* — Pamela F Wu
(74) *Attorney, Agent, or Firm* — JCIPRNET

(57) ABSTRACT

The present invention provides a device for supporting and positioning an endoscope maneuvering system, the device connectable to a fixed support, the device comprising: a. a support mechanism releasably connectable to said endoscope maneuvering system; b. at least one movable arm comprising at least one first jointed connection to said support mechanism, said at least one movable arm adapted to position and orient said endoscope maneuvering system; and c. a base connector comprising at least one second jointed connection to said at least one movable arm, said base connector fixedly connectable to said fixed support; wherein said device is adapted to maintain said endoscope maneuvering system in a state of quasi-static dynamic equilibrium.

17 Claims, 6 Drawing Sheets

(58) Field of Classification Search
CPC ....... A61B 1/0016; A61B 1/313; A61B 34/00;
A61B 2034/301–305; A61B 34/32; A61B
34/35; A61B 34/37; A61B 34/70; A61B
1/00156; A61B 90/50; A61B 90/35–36;
A61B 90/361; A61B 34/30; A61B
2034/302; A61B 34/71; A61B
2034/303–306
USPC ........................................................ 600/102
See application file for complete search history.

(56) References Cited

U.S. PATENT DOCUMENTS

| | | | |
|---|---|---|---|
| 2004/0138524 A1 | 7/2004 | Ueda et al. | |
| 2004/0246469 A1* | 12/2004 | Hirose | A61B 90/50 356/139.03 |
| 2008/0249365 A1* | 10/2008 | Masaki | A61B 1/00149 600/152 |
| 2009/0048611 A1 | 2/2009 | Funda et al. | |
| 2009/0216248 A1* | 8/2009 | Uenohara | A61B 17/29 606/130 |
| 2010/0069920 A1* | 3/2010 | Naylor | A61N 5/1049 606/130 |
| 2010/0274079 A1* | 10/2010 | Kim | A61B 1/00147 600/102 |
| 2011/0071544 A1* | 3/2011 | Steger | A61M 25/0105 606/130 |
| 2011/0238083 A1* | 9/2011 | Moll | A61B 34/76 606/130 |
| 2013/0331644 A1* | 12/2013 | Pandya | A61B 1/00188 600/102 |

\* cited by examiner

SUPPORT AND POSITIONER FOR AN ENDOSCOPE MANEUVERING SYSTEM

FIELD OF THE INVENTION

The present invention generally pertains to a system and method for supporting and maneuvering an endoscope positioning system.

BACKGROUND OF THE INVENTION

Laparoscopic surgery is becoming increasingly popular with patients because the scars are smaller and their period of recovery is shorter. In laparoscopic surgery, the surgeon performs the operation through small holes using long instruments and observing the internal anatomy with an endoscope camera. The endoscope is conventionally held by a camera assistant since the surgeon must perform the operation using both hands.

Laparoscopic surgery requires special training for the surgeon or gynecologist and the theatre nursing staff. The equipment is often expensive and is not available in all hospitals. During laparoscopic surgery, it is often required to shift the spatial placement of the endoscope in order to present the surgeon with an optimal view.

The surgeon's performance is largely dependent on the camera's position relative to the instruments and on a stable image shown by the monitor; also the picture shown must be in the right orientation.

Conventional laparoscopic surgery makes use of either human assistants that manually shift the instrumentation or alternatively robotic automated assistants (such as JP patent No. 06063003). The main problem is the difficulty for the assistant in keeping the endoscope in the right spatial position, holding the endoscope steadily and keeping the scene in the right orientation.

To overcome these problems, several new technologies have been developed, using robots to hold the endoscope while the surgeon performs the procedure, e.g., Lapman, Endoassist, etc. But these technologies are expensive, difficult to install, uncomfortable to use, limit the dexterity of the surgeon and have physical dimension much bigger than all the operating tools. Relative to the required action, they also move in big increments with several arms moving. Another robot, LER, (which was developed by the TEVIC-GMCAO Laboratory) is described in US. Patent Application No. 200/6100501. It consists of a compact camera-holder robot that rests directly on the patient's abdomen and an electronic box containing the electricity supply and robot controllers. LER has relatively small dimensions but has a 110 mm diameter base ring that must be attached, or be very close to, the patient's skin. This ring occupies space over the patient's body, affecting the surgeon's activities: limiting the surgeon's choice of where to place other trocars, changing the surgeon's usual way of making the procedure, sometimes forcing the setup process to be as long as 40 minutes. Also the LER has only 3 degrees of freedom and has no ability to control the orientation of the picture shown to surgeon (the LER cannot rotate the endoscope around its longitudinal axis).

However, even the improved technologies still limit the ability to control the spatial position of an endoscope tube to any orientation during the laparoscopic surgery, such that the surgeon reaches any desired area within the working envelope in the body being operated on and, further, these technologies still permit the endoscope to put pressure on the insertion point of the endoscope into the body, which can cause unwanted movement of the endoscope and can cause damage to the tissue of the patient.

It is therefore a long felt need to provide a support and positioning system for an endoscope maneuvering system that reduces limitations on the range of spacial positions and orientations of the endoscope tube, which reduces mechanical strains on the endoscope maneuvering system and which enables reduction of the pressure exerted on the insertion point by the endoscope tube.

SUMMARY OF THE INVENTION

It is an object of the present invention to disclose a system and method for supporting and positioning an endoscope maneuvering system.

It is another object of the present invention to disclose a device for supporting and positioning an endoscope maneuvering system, the device connectable to a fixed support, the device comprising:
  a. a support mechanism releasably connectable to the endoscope maneuvering system;
  b. at least one movable arm comprising at least one first jointed connection to the support mechanism, the at least one movable arm adapted position and orient the endoscope maneuvering system; and
  c. a base connector comprising at least one second jointed connection to the at least one movable arm, the base connector fixedly connectable to the fixed support
  wherein the device is adapted to maintain said endoscope maneuvering system in a state of quasi-static dynamic equilibrium.

It is another object of the present invention to disclose the device, additionally comprising a vertical elevation mechanism adapted to alter the vertical elevation of the support mechanism.

It is another object of the present invention to disclose the device, wherein the vertical elevation mechanism is an hydraulic mechanism, an electrical mechanism and any combination thereof.

It is another object of the present invention to disclose the device, wherein the support mechanism comprises at least two jointly connected arms; the third jointed connection between the at least two jointly connected arms is characterized by an axis of rotation, and the at least two arms are rotatable by approximately 360° around the axis of rotation.

It is another object of the present invention to disclose the device, wherein at least one of a group consisting of the first jointed connection, the second jointed connection and the third jointed connection comprises at least one joint.

It is another object of the present invention to disclose the device, wherein the jointed connections are hydraulic joints.

It is another object of the present invention to disclose the device, wherein at least one of a group consisting of the first jointed connection, the second jointed connection, and the third jointed connections is lockable to prevent movement thereof.

It is another object of the present invention to disclose the device, wherein the locking of at least one of a group consisting of: the first jointed connection, the second jointed connection, and the third jointed connection is selected from a group consisting of: each joint can be locked individually, all joints are locked simultaneously and any combination thereof.

It is another object of the present invention to disclose the device, wherein the simultaneous locking of all the joints is commanded by at least one selected from a group consisting of: pressing a button, rotating a knob, sliding a slider, moving a lever, emitting a predetermined sound pattern, making a predetermined gesture, touching a touchscreen, touching a touchpad, illuminating a predetermined location, and blocking illumination to a predetermined location.

It is another object of the present invention to disclose the device, wherein the locking of the first, second and third jointed connections is done by at least one of a group consisting of: manually and using a motor.

It is another object of the present invention to disclose the device, wherein the device is adapted to provide counterbalanced support of the endoscope maneuvering system such that the endoscope maneuvering system is effectively in a "floating condition" with minimal net torque around any axis.

It is another object of the present invention to disclose the device, wherein the fixed support is selected from a group consisting of: a hospital bed, and a hospital cart and any combination thereof.

It is another object of the present invention to disclose the device, wherein, by means of the base connector, the device is linkable either releasably or fixedly to the fixed support.

It is another object of the present invention to disclose the device, wherein the position and orientation of the endoscope maneuvering system is automatically adjustable.

It is another object of the present invention to disclose the device, wherein the position and orientation of an endoscope attached to said endoscope maneuvering system is automatically adjustable.

It is another object of the present invention to disclose a method for supporting an endoscope maneuvering system comprising steps of:
  a. providing a device for supporting an endoscope maneuvering system, the device connectable to a fixed support, the device comprising:
     i. a support mechanism;
     ii. at least one movable arm comprising at least one first jointed connection to the support mechanism, the at least one movable arm adapted to position and orient the endoscope maneuvering system; and,
     iii. a base connector comprising at least one second jointed connection to the at least one movable arm;
  b. releasably connecting the endoscope maneuvering system to the support mechanism;
  c. connecting the base connector to the fixed support; and
  d. maneuvering the at least one movable arm; thereby positioning and orienting the endoscope maneuvering system;
wherein step (d) of maneuvering the at least one movable arm is performed whilst maintaining the endoscope maneuvering system in a state of quasi-static dynamic equilibrium.

It is another object of the present invention to disclose the method, additionally comprising steps of altering the vertical elevation of the support mechanism by means of a vertical elevation mechanism.

It is another object of the present invention to disclose the method, additionally comprising steps of selecting the vertical elevation mechanism to be a hydraulic mechanism, an electrical mechanism and any combination thereof.

It is another object of the present invention to disclose the method, additionally comprising steps of providing the support mechanism with at least two jointly connected arms; the third jointed connection between the two jointly connected arms characterized by an axis of rotation, and rotating the at least two arms approximately 360° around the axis of rotation.

It is another object of the present invention to disclose the method, additionally comprising steps of selecting at least one of a group consisting of the first the jointed connection, the second jointed connection and the third jointed connection to be at least one joint.

It is another object of the present invention to disclose the method, additionally comprising steps of locking at least one of a group consisting of the first jointed connection, the second jointed connection and the third jointed connection to prevent movement thereof.

It is another object of the present invention to disclose the method, additionally comprising steps of selecting the locking of at least one of a group consisting of the first jointed connection, the second jointed connection and the third jointed connection from a group consisting of: locking each joint individually, locking all joints simultaneously and any combination thereof.

It is another object of the present invention to disclose the
  method, additionally comprising steps of commanding
  the simultaneous locking of all the joints by at least one
  selected from a group consisting of: pressing a button,
  rotating a knob, sliding a slider, moving a lever, emitting a predetermined sound pattern, making a predetermined gesture, touching a touchscreen, touching a
  touchpad, illuminating a predetermined location.

It is another object of the present invention to disclose the method, additionally comprising steps of selecting the method of locking of at least one of a group consisting of the first jointed connection, the second jointed connection and the third jointed connection to be at least one of a group consisting of: manually and using a motor.

It is another object of the present invention to disclose the method, additionally comprising steps of the device providing counterbalanced support of the endoscope maneuvering system such that the endoscope maneuvering system is effectively in a floating condition with minimal net torque around any axis.

It is another object of the present invention to disclose the method, additionally comprising steps of selecting the fixed support from a group consisting of: a hospital bed, a hospital cart and any combination thereof.

It is another object of the present invention to disclose the method, additionally comprising steps of either releasably or fixedly linking the device to the fixed support by means of the base connector.

It is another object of the present invention to disclose the method, additionally comprising steps of automatically adjusting the position and orientation of the endoscope maneuvering system.

It is another object of the present invention to disclose the method, additionally comprising steps of automatically adjusting the position and orientation of an endoscope attached to the endoscope maneuvering system.

BRIEF DESCRIPTION OF THE FIGURES

In order to better understand the invention and its implementation in practice, a plurality of embodiments will now be described, by way of non-limiting example only, with reference to the accompanying drawings, wherein.

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for supporting a laparoscope positioning system.

The term 'approximately' hereinafter refers to a range of ±25% around a value.

The term 'plurality' hereinafter refers to any number greater than one.

The term 'floating' hereinafter refers to the condition of an object having its weight counterbalanced by the weight of another object, thus minimizing torques and, therefore, pressures, on the moving parts of the floating object.

The term 'quasi-static' hereinafter refers to movement where the movement is slow enough that inertial effects are negligible so that the system reaches equilibrium a time scale much faster than the time scale of the motion. An example of quasi-static motion is loading a spring slowly. After each increment of load, the spring extends smoothly to its final position and the end position of the spring depends solely on Hooke's Law. If, however, the spring is loaded quickly, non-static effects come into play and the end of the spring oscillates about the static rest position.

The term 'dynamic equilibrium' hereinafter refers to equilibrium occurring during movement.

The terms 'laparoscopic maneuvering system', 'endoscopic maneuvering system' and 'laparoscopic positioner' hereinafter refer to a system for maneuvering an endoscope or laparoscope used for laparoscopic surgery. These terms will be used equivalently herein.

In the Figures shown hereinbelow, similar numbers refer to similar items.

The present device provides a support system for a laparoscopic maneuvering system, an endoscopic maneuvering system or a laparoscopic positioner. The support system comprises a plurality of arms, with the arms connected together by lockable joints. At least one of the plurality of arms is lockably and jointedly linked with a base connector enabling the device to be fixedly connected to a fixed support such as a hospital bed, a hospital cart, a shelf or any other means of holding the device immovable relative to the patient during an operation. At least one other arm is lockably and jointedly linked with a support mechanism that realeasably and fixedly supports a laparoscope maneuvering system.

Figure 1A:
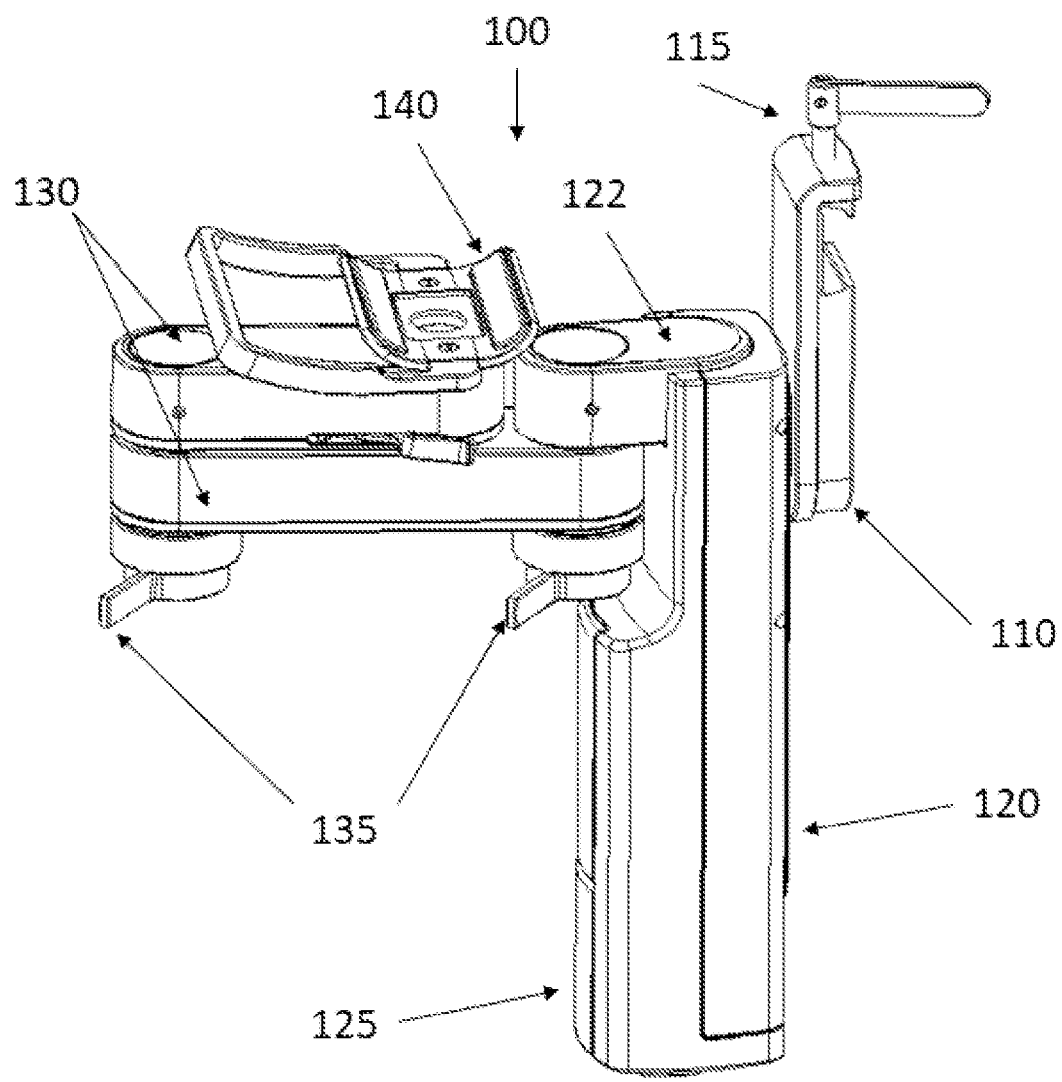
FIG. 1A-B illustrates an embodiment of the device to support and position an endoscope maneuvering system.
Figure 1B:
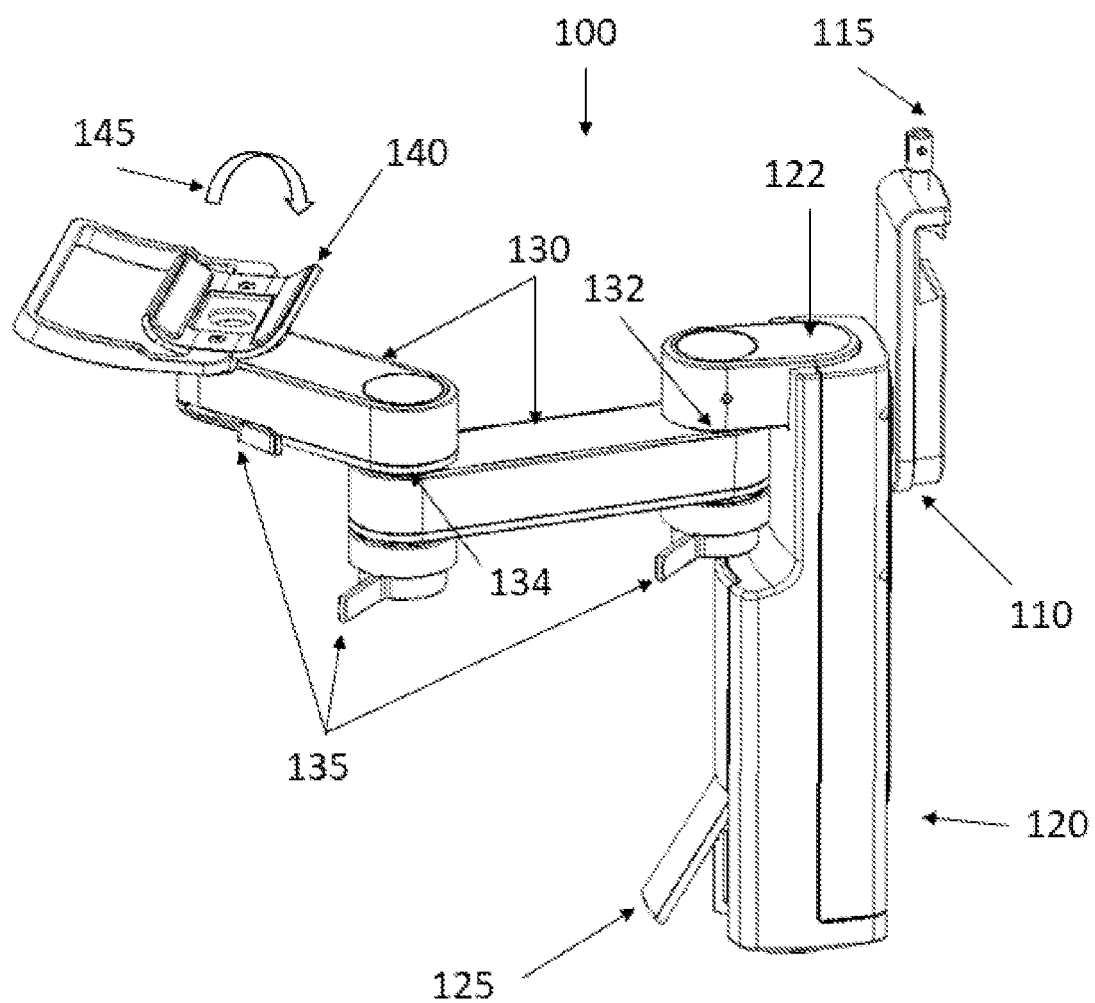

FIG. 1 shows an embodiment of the present device (100). FIG. 1A shows the device in a compact position, with all the arms retracted, while FIG. 1B shows it in an extended position. In this embodiment, the device 100 comprises a clamping mechanism 110 adapted to clamp the support system to a hospital bed. The clamping mechanism is tightened by a screw 115. Fixedly attached to the clamping mechanism is a base unit 120 which can be raised or lowered relative to the clamp, with foot lever 125 providing a means of control of the height. The mechanism (not shown) enabling the height changes can be unpowered (e.g. a spring-and-ratchet mechanism) or can be powered (e.g. a motor). The base unit comprises a section 122 able to be raised or lowered, and is connected via a joint mechanism 132 to the first of the arms 130. Joint mechanism 132 is lockable via first handle 135 at the base of joint mechanism 132. At the other end of the first arm 130 there is a second joint (134) connecting the first arm 130 to a second arm 130. Second joint 134 is lockable via second handle 135. Second arm 130 is jointly connected to the support mechanism (140) for the endoscope maneuvering system (not shown); the joint (not shown) is lockable via the third handle 135. The joint allows rotation of support mechanism 140 about an axis substantially parallel to the longitudinal axis of second arm 130, in the direction shown schematically by arrow 145. Thus all of the joints in the system are manually adjustable and are individually lockable.

In preferred embodiments, each arm has at least one axis of rotation and the arms are capable of rotating a full 360° around each axis of rotation.

In some embodiments, a single joint provides the full 360° rotation around at least one axis.

In other embodiments, the full 360° rotation is achieved by a plurality of joints such that the plurality of joints provides the full 360° of movement. For non-limiting example, a set of three joints, each capable of allowing rotation of 120° around the same axis, would provide the desired full 360° of rotation around the axis.

Figure 2:
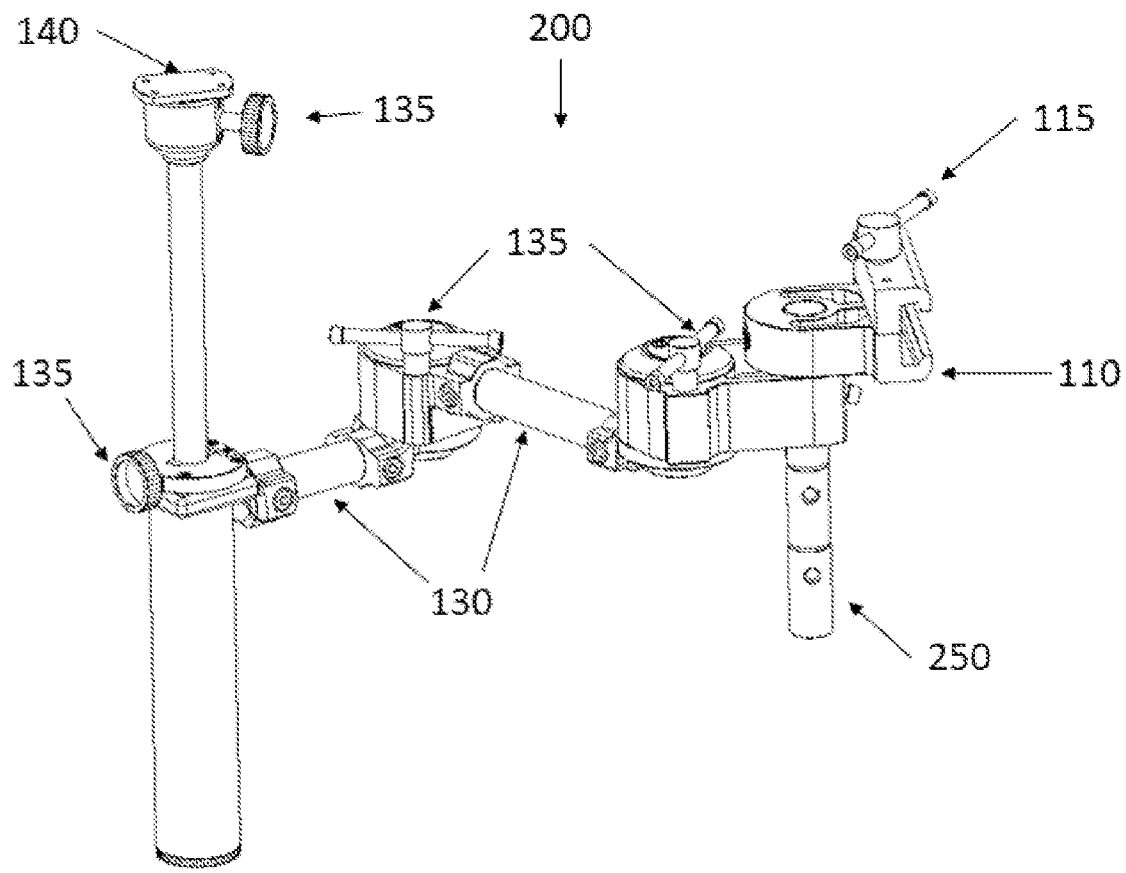
FIG. 2 illustrates an embodiment of the device to support and position an endoscope maneuvering system.

FIG. 2 shows another embodiment (200) of the system. This embodiment also has two arms 130, a clamping mechanism (110) with tightening screw 115, handles 135 and a support mechanism 140 to fixedly hold the endoscope maneuvering system (not shown). In this and the other described embodiments, the support mechanism 140 may take the form of a platform, as shown in FIGS. 2, 1A and 1B. The height of the endoscopic maneuvering system is adjusted via adjustment mechanism 250.

Use of the support system of the present device in positioning the endoscope maneuvering system has several functions. One is to place the maneuvering system in a position whereby the maneuvering system itself will not interfere with the movements of the physician. Another is to enable the operator to orient the endoscope maneuvering system such that it is unlikely that the maneuvering system will be near the end of its travel in any direction at any time during the operation. A third is to orient the maneuvering system such that its weight is counterbalanced by the weight of the support system.

In some embodiments, automatic control, either wired or, preferably, wireless, of the position and orientation of the support system is also enabled. In such embodiments, the endoscope maneuvering system is fixed to the support mechanism 140 and positioned near the center of the maneuvering system's travel, with the laparoscope and endoscope in a zoom-out position. The operator then instructs the control system to adjust the position of the support mechanism until the endoscope maneuvering system is in a position such that it will minimally interfere with the movements of the physician during the operation, and to adjust the orientation of the endoscope maneuvering system until the endoscope maneuvering system is "floating"—its weight being counterbalanced by the weight of the support system, thus minimizing torques and, therefore, pressures, on the moving parts of the endoscope maneuvering system. When a satisfactory position has been found, either manually or under computer control or both, the support system can be locked in place, preventing unwanted movements of the support system during the operation.

In some embodiments, locking of the support system is via the foot lever 125 and handles 135. In other embodiments, a single command simultaneously locks all position and orientation adjusters such as the joints and the vertical positioning systems such as that in base unit 120. In preferred embodiments, both locking via handles and locking via a single command are enabled. The command can be issued by pressing a button, rotating a knob, sliding a slider, moving a lever, via a predetermined sound pattern (a voice command), by a predetermined gesture, by touching a predetermined location such as, but not limited to, a touchscreen or touchpad, by illuminating a predetermined location, or by blocking illumination to a predetermined location such as, but not limited to, a photoelectric device.

Figure 3:
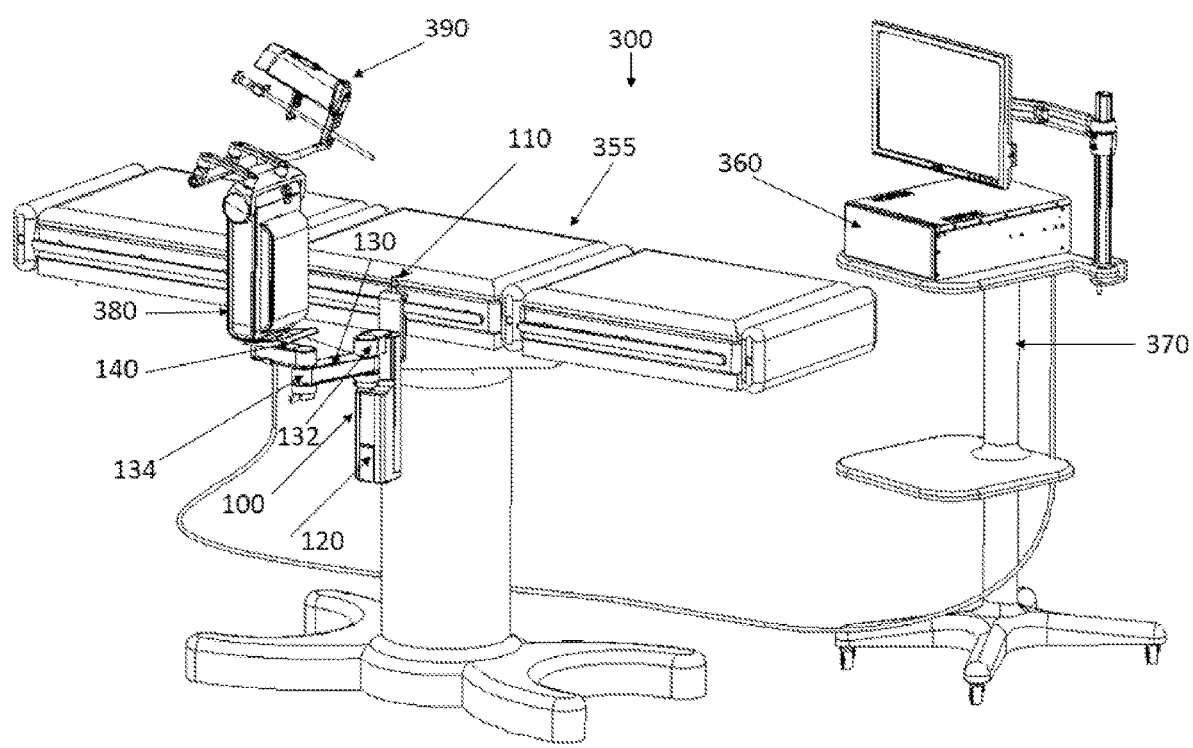
FIG. 3 illustrates an embodiment of the device in use.

FIG. 3 shows an embodiment of the device 100 in use, according to one embodiment of a system for using the device. The device 100 is attached via clamp 110 to a hospital bed 355. The device's base unit 120, arms (130, 138), and support mechanism 140 are in a deployed position, with the endoscope maneuvering system 380 attached to the support mechanism 140, connection between the support mechanism 140 and endoscope maneuvering system selected from a group consisting of a slideable connection, a screwable connection, a lockable connection and any combination thereof. An endoscope 390 is attached to the maneuvering system 380. A hospital cart 370, which can also hold the device when not in use, supports a computerized control system 360 which can control the maneuvering system. In some embodiments, the computerized control system 360 tan lock the joints (132, 134, 136) of the device. In preferred embodiments, the computerized control system 360 can control the elevation mechanism in base unit 120 and, in some preferred embodiments, it can lock the elevation mechanism in base unit 120. In some embodiments, the computerized control system 360 is further able to control the positions and orientations of the joints (132, 134, 136), the joints having axes of rotation (131, 133).

In preferred embodiments, motorized control of the position and orientation is provided for all of the at least four degrees of freedom (joints 132 and 134 between the arms, lifting mechanism in base unit 120, and the joint between second arm 130 and support mechanism 140).

Figure 4A:
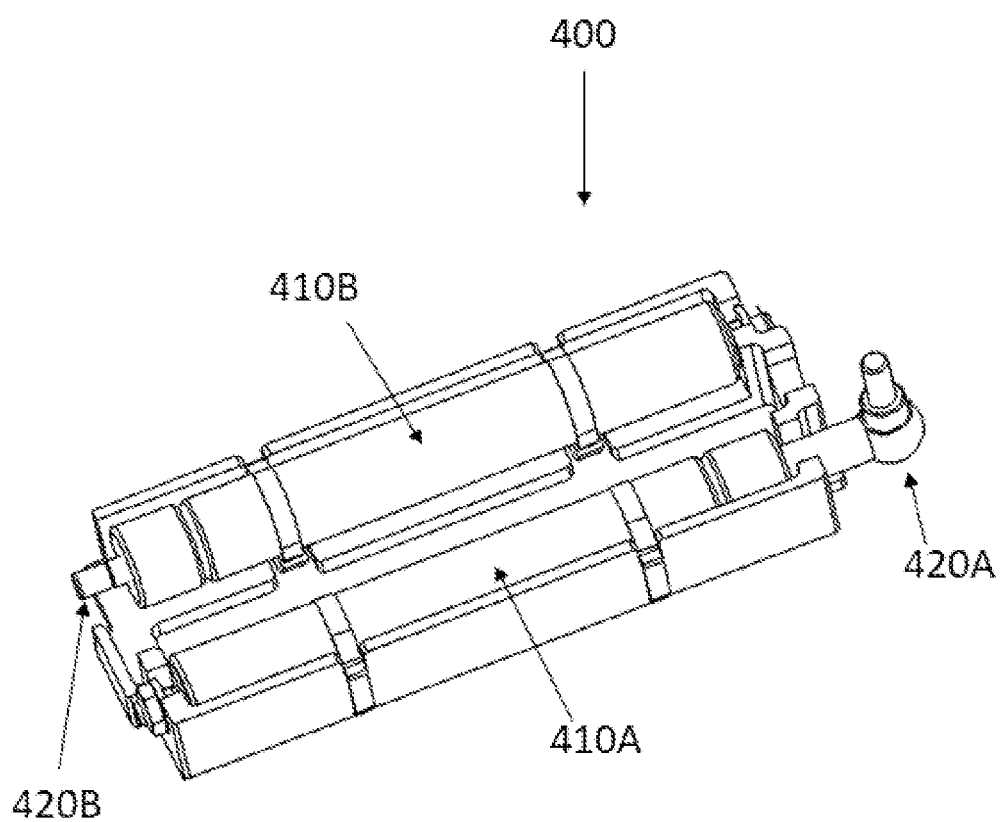
FIG. 4A-B illustrates an embodiment of a lifting mechanism for the device.
Figure 4B:
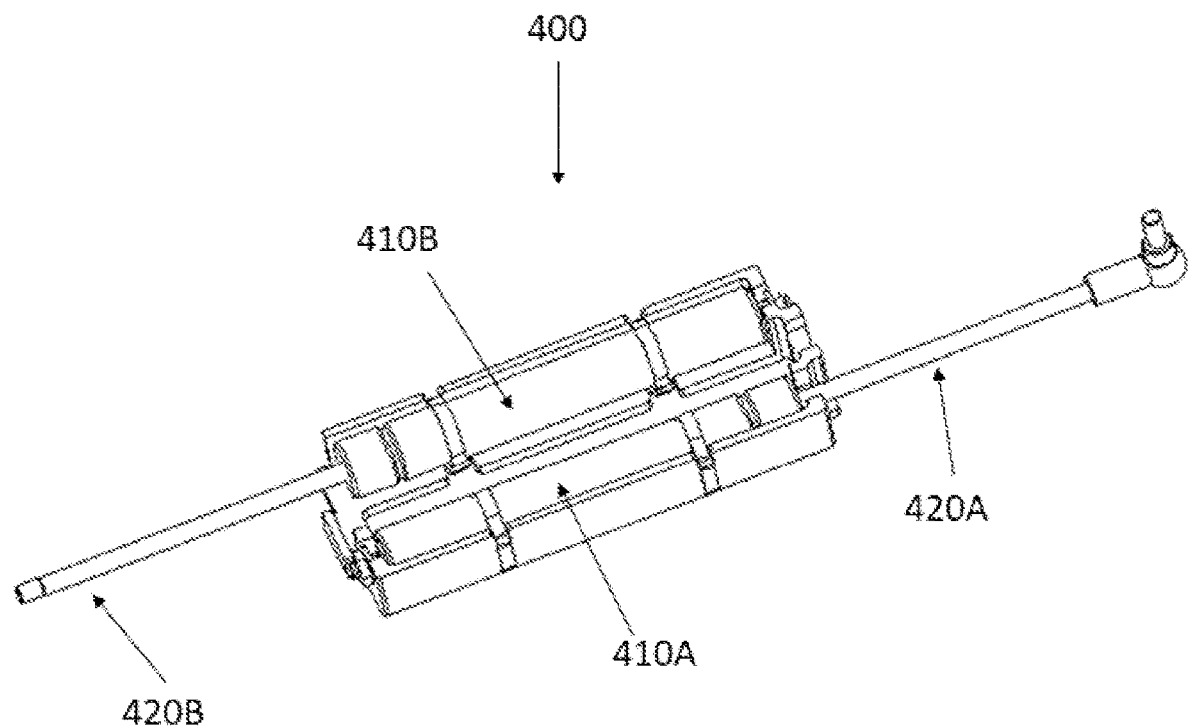

In preferred embodiments, the vertical elevation mechanism in base unit 120 that raises and lowers the device 100 relative to clamp 110 and therefore raises and lowers the endoscope maneuvering system 380 relative to the bed 355 and the patient comprises a hydraulic mechanism. One embodiment of the hydraulic lifting mechanism that enables raising and lowering of the base unit 120 relative to clamp 110 is shown in FIG. 4. In FIG. 4A, the hydraulic lifting mechanism is shown closed, while in FIG. 4B, it is shown open. In the embodiment of FIG. 1, the lifting mechanism will be closed (as shown in FIG. 4A) when the device 100 is at the top of its travel and the lifting mechanism will be open (as shown in FIG. 4B) when the device 100 is at the bottom of its travel.

The hydraulic mechanism comprises two hydraulic pistons 410. Each piston is attached to a rod 420. The outer end of the first rod 420A is connected with a fixed position on the interior of base unit 120, while the outer end of the second rod 420B is fixedly connected to the lifting unit 122. Adding fluid to the pistons pushes the rods outward, thereby raising the base unit 120. Since the pistons 410 are fluidly connected, the pressure tending to force the rods 420 outward is the same for both pistons 410, thereby ensuring that the pressure on the rods is the same, so that a balanced force is exerted on the rods 420. If an unbalanced force is exerted on, for example, the second rod 420B from endoscope maneuvering system 380, fluid will redistribute between first piston 410A and second piston 410B, thereby minimizing unwanted forces and torques on the endoscope maneuvering system 380 and ensuring that endoscope maneuvering system 380 remains in a "floating" condition.

In some embodiments, once the endoscope maneuvering system and endoscope are connected to the support and positioning device of the present invention and the device is coupled to a fixed support such as a hospital bed, the computerized control system adjusts the positions and orientations of the arms of the present device and the height of the support mechanism via motorized control of the joints and the lifting unit so that, when the endoscope maneuvering system is positioned for operation, the torques exerted on the endoscope maneuvering system due to the endoscope are balanced by the torques exerted on the endoscope maneuvering system due to the present device, the torques acting through the fixing connections between the support mechanism and the endoscope maneuvering system.

In some embodiments, once the endoscope maneuvering system and endoscope are connected to the support and positioning device of the present invention and the device is coupled to a fixed support such as a hospital bed, the computerized control system adjusts the positions and orientations of the arms of the present device and the height of the support mechanism via motorized control of the joints and the lifting mechanism so that the automatically adjusts the position and orientation of the endoscope maneuvering system so as to minimize pressure on the patient penetration point, the location on the patient's body where the endoscope or the laparoscope enters the patient's body.

The invention claimed is:

1. A device for supporting and positioning an independent endoscope maneuvering system, the device connectable to a fixed support, the device comprising:
   a first moveable arm;
   an endoscope maneuvering system support platform at a distal end of said first moveable arm, said endoscope maneuvering system support platform rotatable relative to the first moveable arm at a first joint characterized by a first axis of rotation, said endoscope maneuvering system support platform having a longitudinal axis and being connectable to said independent endoscope maneuvering system and configured to fixedly hold said independent endoscope maneuvering system;
   a second moveable arm at a proximal end of said first moveable arm, said first moveable arm rotatable relative to the second moveable arm at a second joint characterized by a second axis of rotation parallel to the first axis of rotation, said first and second moveable arms and said endoscope maneuvering system support platform configured to position and orient said independent endoscope maneuvering system; and
   a base connector at a proximal end of said device, said base connector comprising at least one base-end jointed connection to said second movable arm, said base connector fixedly connectable to said fixed support;
   wherein the endoscope maneuvering system support platform and the first and second moveable arms are moveable relative to the first and second joints between a compact position in which the first and second axes of rotation are parallel to each other and in which the longitudinal axis of the endoscope maneuvering system support platform is parallel to longitudinal axes of the first and second movable arms, and an extended position in which the first and second axes of rotation are parallel to each other and in which the longitudinal axis of the endoscope maneuvering system support platform extends angularly to a longitudinal axis of at least one of the first and second movable arms;

further wherein said independent endoscope maneuvering system is attachable to and releasable from said endoscope maneuvering system support platform, said device is configured to maintain said independent endoscope maneuvering system in a state of quasistatic dynamic equilibrium during maneuvering of the at least one moveable arm, said maintaining by adjustment of the position and orientation of the joints;

wherein the first moveable arm includes an upper surface, and wherein in the compact position the endoscope maneuvering system support platform is disposed above the upper surface.

2. The device according to claim 1, additionally comprising a vertical elevation mechanism configured to alter the vertical elevation of said endoscope maneuvering system support platform relative to the fixed support by raising or lowering the first and second moveable arms relative to the base connector, said vertical elevation mechanism selected from a group consisting of a spring-and-ratchet mechanism, a motor, a hydraulic lifting mechanism, and any combination thereof.

3. The device according to claim 2, wherein said vertical elevation mechanism is a hydraulic mechanism, an electrical mechanism, and any combination thereof.

4. The device according to claim 1, wherein said first moveable arm is rotatable by approximately 360° around said second axis of rotation.

5. The device according to claim 1, wherein said at least one base-end jointed connection comprises a third joint characterized by a third axis of rotation parallel to the first and second axes of rotation.

6. The device according to claim 5, wherein at least one of the first, second, and third joints is lockable to prevent movement thereof.

7. The device according to claim 6, wherein the first, second, and third joints are independently lockable.

8. The device according to claim 6, wherein said locking of said at least one joint is done manually or using a motor.

9. The device according to claim 5, wherein the first, second, and third joints are simultaneously lockable, and wherein said simultaneous locking is commanded by at least one selected from a group consisting of: pressing a button, rotating a knob, sliding a slider, moving a lever, emitting a predetermined sound pattern, making a predetermined gesture, touching a touchscreen, touching a touchpad, illuminating a predetermined location, and blocking illumination to a predetermined location.

10. The device according to claim 1, wherein said device is configured for providing counterbalancing support of said independent endoscope maneuvering system by adjustment of the position and orientation of the joints such that said independent endoscope maneuvering system is effectively in a "floating condition" with minimal net torque on moving parts of the endoscope maneuvering system.

11. The device according to claim 1, wherein said fixed support is selected from a group consisting of: a hospital bed, and a hospital cart, and any combination thereof.

12. The device according to claim 1, wherein, by means of said base connector, said device is linkable either releasably or fixedly to said fixed support.

13. The device according to claim 1, wherein the position and orientation of said independent endoscope maneuvering system is automatically adjustable.

14. The device according to claim 1, wherein the position and orientation of an endoscope attached to said independent endoscope maneuvering system is automatically adjustable.

15. The device according to claim 1, wherein said connection between said endoscope maneuvering system support platform and said independent endoscope maneuvering system selected from a group consisting of a slideable connection, a screwable connection, a lockable connection and any combination thereof.

16. The device according to claim 1, wherein in the compact position the longitudinal axis of the endoscope maneuvering system support platform occupies a common plane with the longitudinal axes of the first and second movable arms.

17. The device according to claim 16, wherein in the compact position the longitudinal axis of the endoscope maneuvering system support platform is vertically aligned with the longitudinal axes of the first and second movable arms.

* * * * *